(12) United States Patent
Li et al.

(10) Patent No.: US 9,044,203 B2
(45) Date of Patent: Jun. 2, 2015

(54) DEVICE FOR ATTACHING TO LUMEN WALL

(75) Inventors: Xiangdong Li, Chongqing (CN); Jian Yuan, Chongqing (CN); Lin Chen, Chongqing (CN); Zhijun Li, Chongqing (CN); Wanli Tong, Chongqing (CN)

(73) Assignee: Chongqing Jinshan Science & Technology (Group) Co., Ltd., Chongqing (CN)

( * ) Notice: Subject to any disclaimer, the term of this patent is extended or adjusted under 35 U.S.C. 154(b) by 368 days.

(21) Appl. No.: 13/462,784

(22) Filed: May 2, 2012

(65) Prior Publication Data

US 2012/0277598 A1    Nov. 1, 2012

Related U.S. Application Data

(63) Continuation-in-part of application No. PCT/CN2010/001708, filed on Oct. 27, 2010.

(51) Int. Cl.
*A61B 5/02* (2006.01)
*A61B 5/00* (2006.01)

(52) U.S. Cl.
CPC .......... *A61B 5/6876* (2013.01); *A61B 5/6884* (2013.01)

(58) Field of Classification Search
CPC .. A61B 17/1285; A61B 17/10; A61B 17/122; A61B 2017/2926; A61B 2017/306; A61B 17/083; A61B 17/085; A61B 5/6884; A61B 5/6876; A61F 5/0086
See application file for complete search history.

(56) References Cited

U.S. PATENT DOCUMENTS

| | | | | |
|---|---|---|---|---|
| 5,871,488 A | * | 2/1999 | Tovey et al. | 606/139 |
| 2008/0249560 A1 | * | 10/2008 | Stokes et al. | 606/213 |
| 2011/0077668 A1 | * | 3/2011 | Gordon et al. | 606/142 |
| 2011/0105839 A1 | * | 5/2011 | Hoffman et al. | 600/104 |

FOREIGN PATENT DOCUMENTS

| | | |
|---|---|---|
| AU | 2010312210 B2 | 9/2013 |
| CN | 101278856 A | 10/2008 |
| JP | H06-142081 A | 5/1994 |

OTHER PUBLICATIONS

Patent Examination Report No. 1 (Office Action) issued Nov. 26, 2012, by the Australian Patent Office in corresponding Australian Patent Application No. 2010312210 (3 pages).
Notice of Acceptance issued Sep. 11, 2013, by the Australian Patent Office in corresponding Australian Patent Application No. 2010312210 (2 pages).

\* cited by examiner

*Primary Examiner* — Gary Jackson
*Assistant Examiner* — Scott T Luan
(74) *Attorney, Agent, or Firm* — Osha Liang LLP

(57) ABSTRACT

A fixing device for attaching to a lumen wall, the device including a base (18) and a fixing mechanism (5) fixed on the base (18). The fixing mechanism (5) includes a housing (5*a*), at least a set of clamping brackets (3), and a rotating shaft (7). A bracket hole (3*b*) is formed on each clamp bracket (3), and the rotating shaft (7) passes through the bracket hole (3*b*) and fixes each set of the clamping brackets (3) on the housing (5*a*) of the fixing device.

9 Claims, 20 Drawing Sheets

DEVICE FOR ATTACHING TO LUMEN WALL

CROSS-REFERENCE TO RELATED APPLICATIONS

This application is a continuation-in-part of International Patent Application No. PCT/CN2010/001708 with an international filing date of Oct. 27, 2010, designating the United States, now pending, and further claims priority benefits to Chinese Patent Application No. 200910207950.0 filed Nov. 2, 2009. The contents of all of the aforementioned applications, including any intervening amendments thereto, are incorporated herein by reference.

BACKGROUND OF THE INVENTION

1. Field of the Invention

The invention relates to a fixing device for intravital lumen.

2. Description of the Related Art

With the miniaturization of devices, it is practical and useful to fix a small apparatus to living tissue for the detection of a variety of vital signs and treatment for physiological diseases.

A conventional method for attaching an apparatus to a tissue includes puncturing the tissue by means of a needle with axis movement. Although it is able to fix the apparatus to the tissue, the axial rotation of the apparatus in the tissue cannot be avoided, which results in a sensitive portion of the apparatus or even the apparatus for treating components away from the tissue, and may cause the problems such as the instability of monitoring data, the increased risks of misrepresentation or incorrect targeting of the part requiring treatment.

The prior art also provides a method for fixing the tissue using one single point, although this method can realize the fixing of the tissue, it may still result in fixation failure when the tissue is sliding.

SUMMARY OF THE INVENTION

In view of the above-described problems, it is one objective of the invention to provide a fixing device for intravital lumen that can avoid of the axial rotation of apparatus in a tissue and ensure that the apparatus cannot be affected by the sliding of the tissue.

To achieve the above objective, one embodiment of the invention provides a fixing device for intravital lumen, comprising a base, and a fixing mechanism fixed on the base, wherein the fixing mechanism comprises a housing, at least a set of clamping brackets, and a rotating shaft; a bracket hole is formed on each clamping bracket, and the rotating shaft passes through the bracket holes and fixes each set of the clamping brackets on the housing of the fixing device; a passage is formed on the housing for allowing the entry and exit of a force acting mechanism, and a through hole is formed on the base for allowing gas to enter the fixing mechanism; and when the fixing device for intravital lumen is placed inside an intravital lumen, the gas is extracted through the through hole, and a soft tissue of intravital lumen enters a clearance space between a pair of clamping brackets, and a force is acted on back ends of at least a pair of the clamping brackets and causes the clamping brackets to rotate around the rotating shaft; and with the rotation of the clamping brackets, the opening degree of two front ends of a pair of the clamping brackets becomes smaller, which causes the soft tissue in the clearance space to be squeezed and clamped; when the clamping brackets clamp, an intravital tissue is squeezed and enclosed in a small space, which causes the fixing device to be fixed on the wall of intravital tissue.

In a class of this embodiment, each clamping bracket comprises a stop mechanism disposed thereon; when a pair of the clamping brackets clamp, the intravital tissue is squeezed and enclosed in a small space, meanwhile, clamping brackets are locked by the stop mechanism.

In a class of this embodiment, the force acted on the back ends of the clamping brackets is generated by the force acting mechanism or by a medical string.

In a class of this embodiment, the fixing device further comprises a compression spring connected to the back ends of a pair of clamping brackets and a stop bolt; a first stop hole formed on the housing, and a second stop hole formed on each the clamping bracket; when the fixing device is placed outside the intravital lumen, the stop bolt stays in both a first stop hole and a second stop hole; the compression spring is in compression state, and two front ends of a pair of the clamping brackets are at opening position; after the fixing device is placed inside the intravital lumen, the gas is extracted through the through hole, and the soft tissue of the intravital lumen enters the clearance space; a tension force generated by the compression spring is acted on the back ends after the stop bolt is pulled out from the first stop hole and the second stop hole, which closes the back ends of the clamping brackets, causes two front ends of a pair of the clamping brackets to rotate around the rotating shaft and clamp, and causes the intravital tissue to be squeezed and enclosed in the clearance space, and further causes the fixing device to be fixed on the wall of the intravital tissue.

In a class of this embodiment, when the fixing mechanism comprises a set of clamping brackets, each set of clamping brackets comprise at least a pair of clamping brackets; when the fixing mechanism comprises at least two sets of clamping brackets, each set of clamping brackets comprises one or more pairs of clamping brackets; and the back ends of all the clamping brackets are connected to each other through a medical string, in order to work together under an acting force.

In a class of this embodiment, the base comprises a detecting head for data acquisition, or a treating mechanism, and a wireless transmission unit, the detecting head or treating mechanism is in fixed connection with the wireless transmission unit, and is exposed outside the fixing device.

In a class of this embodiment, the fixing device further comprises a releasing seat, through which the fixing mechanism is fixed on a releasing means.

In a class of this embodiment, the releasing means comprises a connecting seat, a sealing washer, a guiding pipe, a clamping mechanism, and a handle; and a movable operating bolt and a gas inlet are disposed on the handle; and the guiding pipe is connected with the handle; a movable force acting string passes through the guiding pipe and the sealing washer to be fixed on a sealing seat, and the sealing seat is connected with the clamping mechanism; the clamping mechanism is embedded in the connecting seat; and the connecting seat comprises a sliding groove which allows the clamping mechanism to slide in.

In a class of this embodiment, the clamping mechanism comprises at least two transformable or movable clamping clacks; the clamping clacks, are in movable connection with two grooves, of the releasing seat; and the fixing mechanism is fixed on the connecting seat through the releasing seat and the clamping mechanism; a relative movement is formed between the clamping mechanism and the connecting seat, which causes the clamping clacks, to be disengaged from the grooves, of the releasing seat, and further causes the releasing means to be disengaged from the fixing mechanism, thereby releasing the fixing mechanism.

In a class of this embodiment, the clamping mechanism further comprises a fixing shaft, a supporting shaft, a first releasing spring, and a second releasing spring; the clamping clacks and are fixed on the connecting seat through the fixing shaft; after a supporting shaft is extracted, the clamping clacks, are pushed by releasing springs, and rotate around the fixing shaft, which enlarges the gap between the clamping clack and causes the clamping clacks, to be disengaged from the grooves.

In a class of this embodiment, the clamping mechanism further comprises a supporting shaft, a first releasing spring, and a second releasing spring; the clamping clacks, are fixed on the connecting seat through a supporting shaft and releasing strings; after the supporting shaft is extracted, the clamping clacks, are pushed by the releasing strings, and move towards the connecting seat, which enlarges the gap between the clamping clacks and causes the clamping clacks to be disengaged from the grooves.

In a class of this embodiment, the clamping mechanism further comprises a fixing shaft, pulling component, and releasing spring; the clamping clacks, are fixed on the connecting seat through the fixing shaft; and when the pulling component is pulled, the clamping clacks, start to rotate around the fixing shaft, which enlarges the gap between the clamping clacks, and causes the clamping clacks, to be disengaged from the grooves.

Advantages of the invention are summarized below. The fixing device is fixed at multiple points on the wall of intravital lumen, which provides a restriction to the axial rotation of such device in the lumen, enhances the reliability of fixation, and improves the accuracy of locating of device.

DETAILED DESCRIPTION OF THE EMBODIMENTS

For further illustrating the invention, experiments detailing a fixing device for intravital lumen are described below. It should be noted that the following examples are intended to describe and not to limit the invention.

Figure 1:
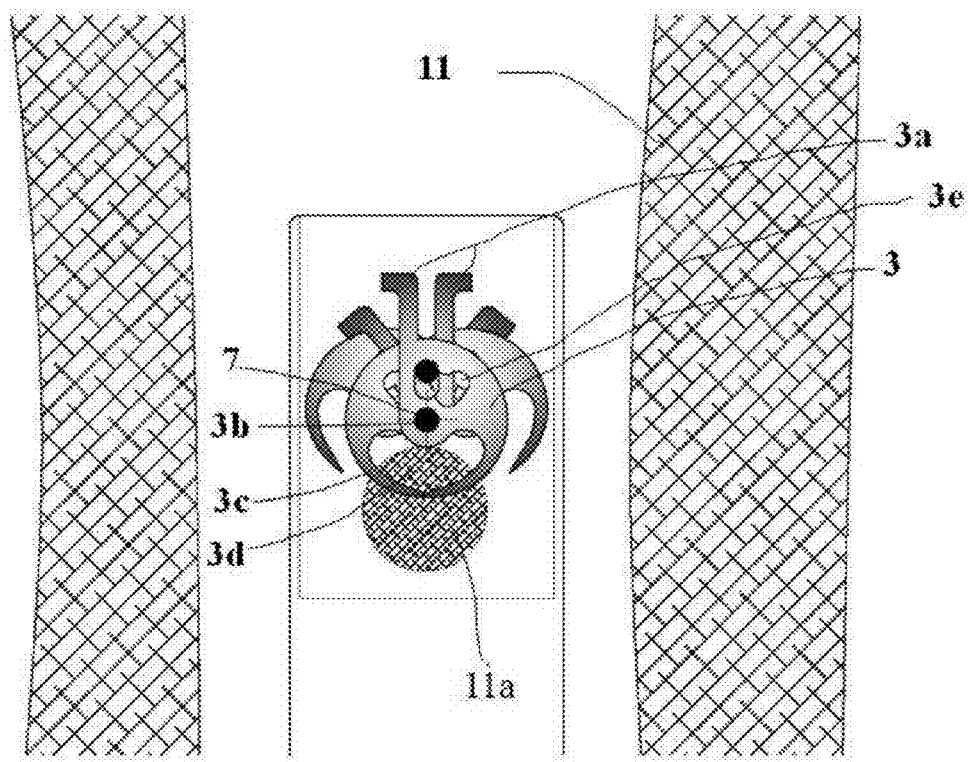
FIG. 1 illustrates one embodiment of the invention, in which several pairs of clamping brackets narrow the gap through rotation, so as to cause a fixing device to clamp on the surface of a tissue.

To provide a clear description of the principle of clamping, FIG. 1 illustrates one embodiment of the invention, in which the gap between a pair of clamping brackets 3 is narrowed through rotating the clamping brackets, so as to cause the fixing device to clamp on the surface of the tissue. In FIG. 1, one set of clamping brackets comprise several pairs of clamping brackets. Each pair of clamping brackets 3 are at their open position before clamping, and a clearance space is formed between the front ends 3c of a pair of clamping brackets. The size of the space is determined by the opening degree of a pair of clamping brackets 3.

In FIG. 1, the clamping brackets 3 are fixed on a rotating shaft 7, and each clamping bracket 3 comprises a front end 3c, a bracket hole 3b, a back end 3a, and a stop mechanism 3e.

When the clamping brackets 3 are placed at a specific position where data detection and treatment are required for the intravital tissue, the clamping brackets 3 contact the intravital lumen 11, the tissue 11a of lumen enters a clearance space 3d, and when a force is acted on the back end of the clamping bracket 3 by a clamping mechanism, such clamping bracket 3 starts to rotate around the rotating shaft 7. With the rotation of clamping bracket 3, the opening degree of the front ends 3c of a pair of the clamping brackets 3 becomes smaller, which causes the tissue 11a in the clearance space to be squeezed and clamped.

When the clamping brackets 3 clamp, the tissue is squeezed and enclosed in a tiny space, and then the clamping brackets 3 are locked by the stop mechanism 3e.

Figure 2:
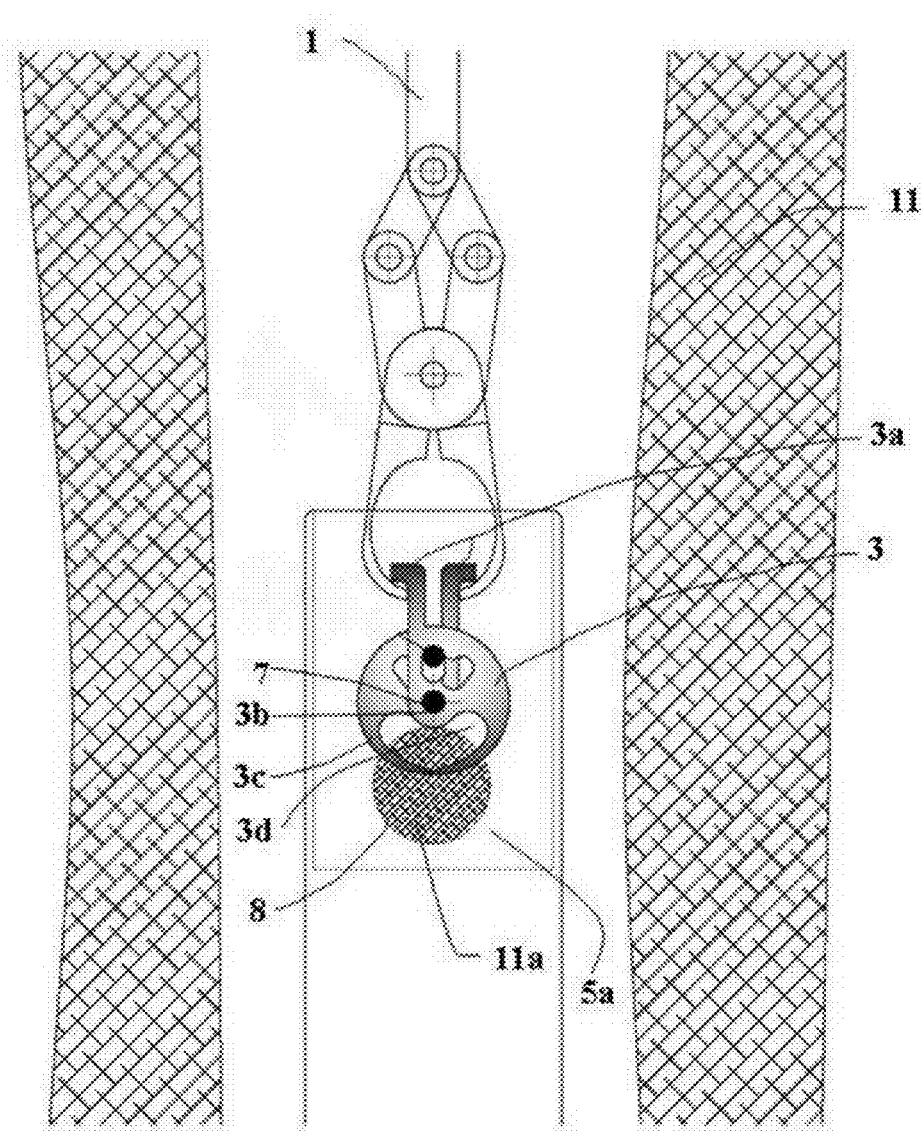
FIG. 2 illustrates one embodiment of the invention, in which several clamping brackets are operated through an external general clamping mechanism to cause a fixing device to clamp on the surface of a tissue.

FIG. 2 illustrates one embodiment of the invention, in which several clamping brackets 3 are operated through an external general clamping mechanism 1 to cause the fixing device to clamp on the surface of the tissue 11.

Figure 3A:
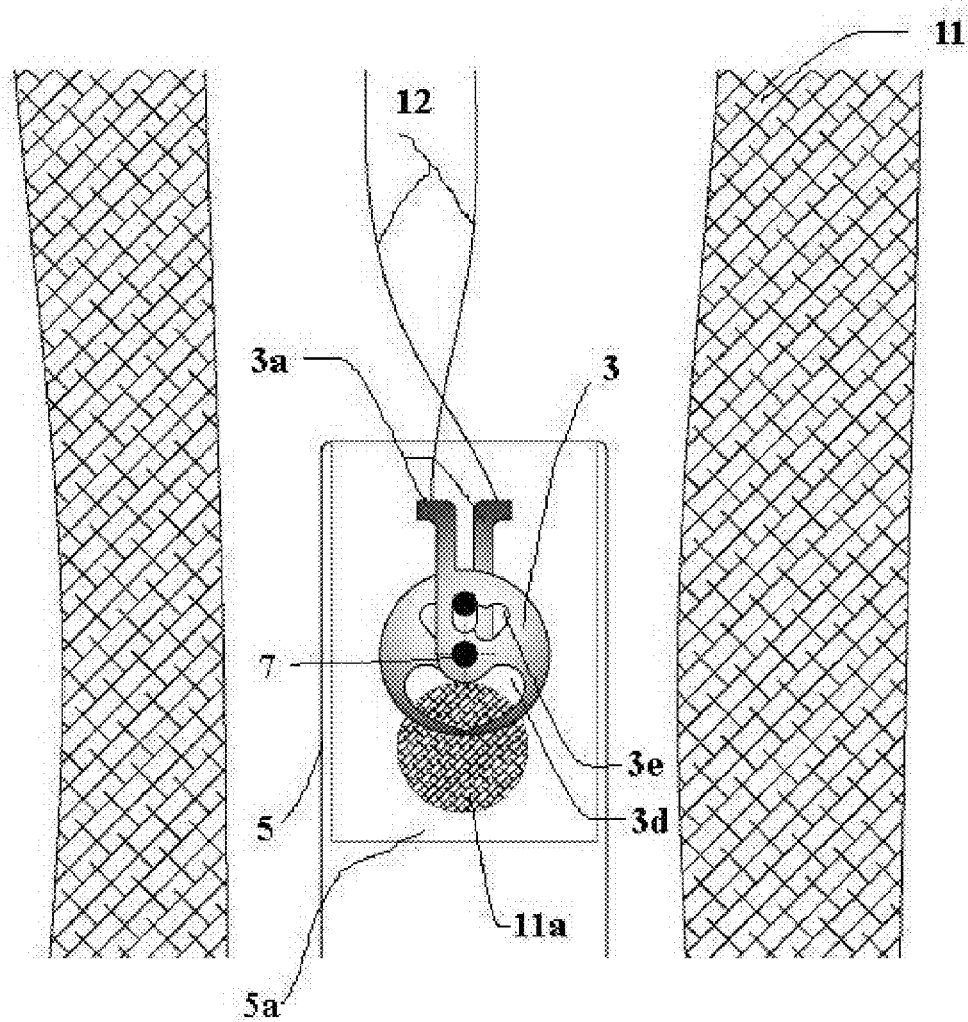
FIG. 3a illustrates one embodiment of the invention, in which several clamping brackets are operated through a medical string to cause a fixing device to clamp a tissue.

FIG. 3a illustrates one embodiment of the invention, in which several clamping brackets 3 are operated through a medical string 12 to cause the fixing device to clamp the tissue 11.

Figure 3B:
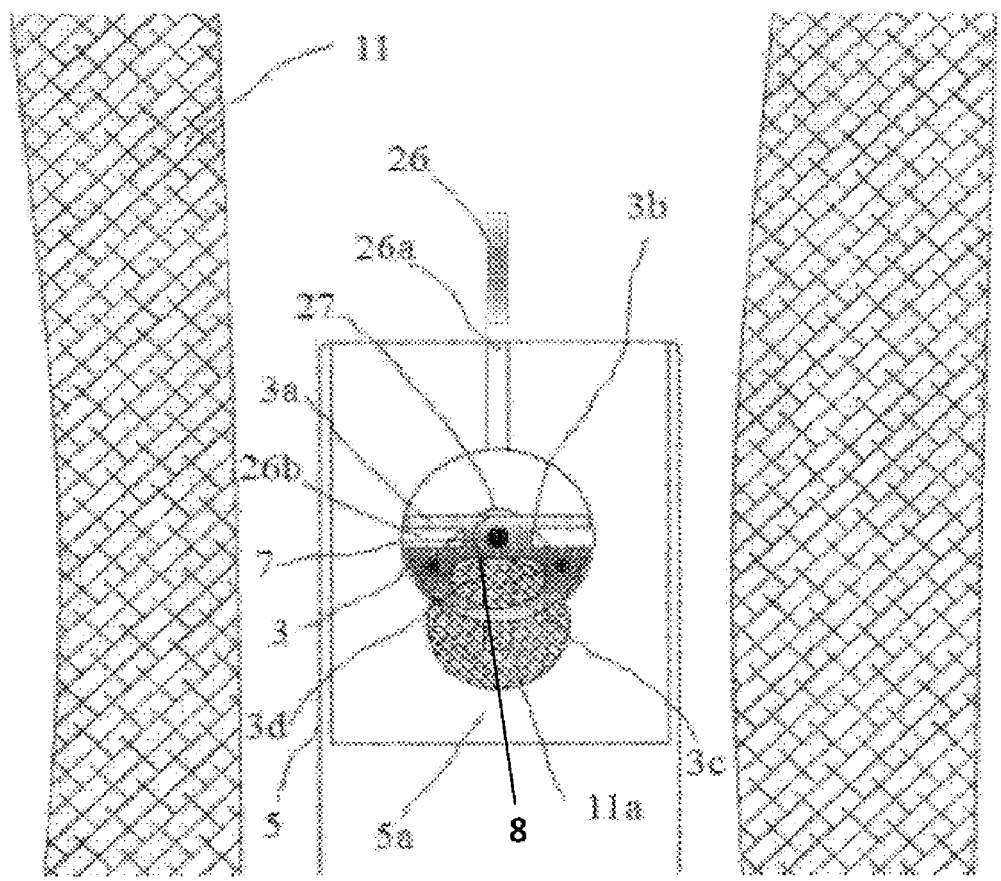
FIG. 3b illustrates one embodiment of the invention, in which several clamping brackets are operated through a compression spring to cause a fixing device to clamp a tissue.

FIG. 3b illustrates one embodiment of the invention, in which several clamping brackets 3 are operated through a compression spring 27 to cause the fixing device to clamp the tissue 11.

Figure 4:
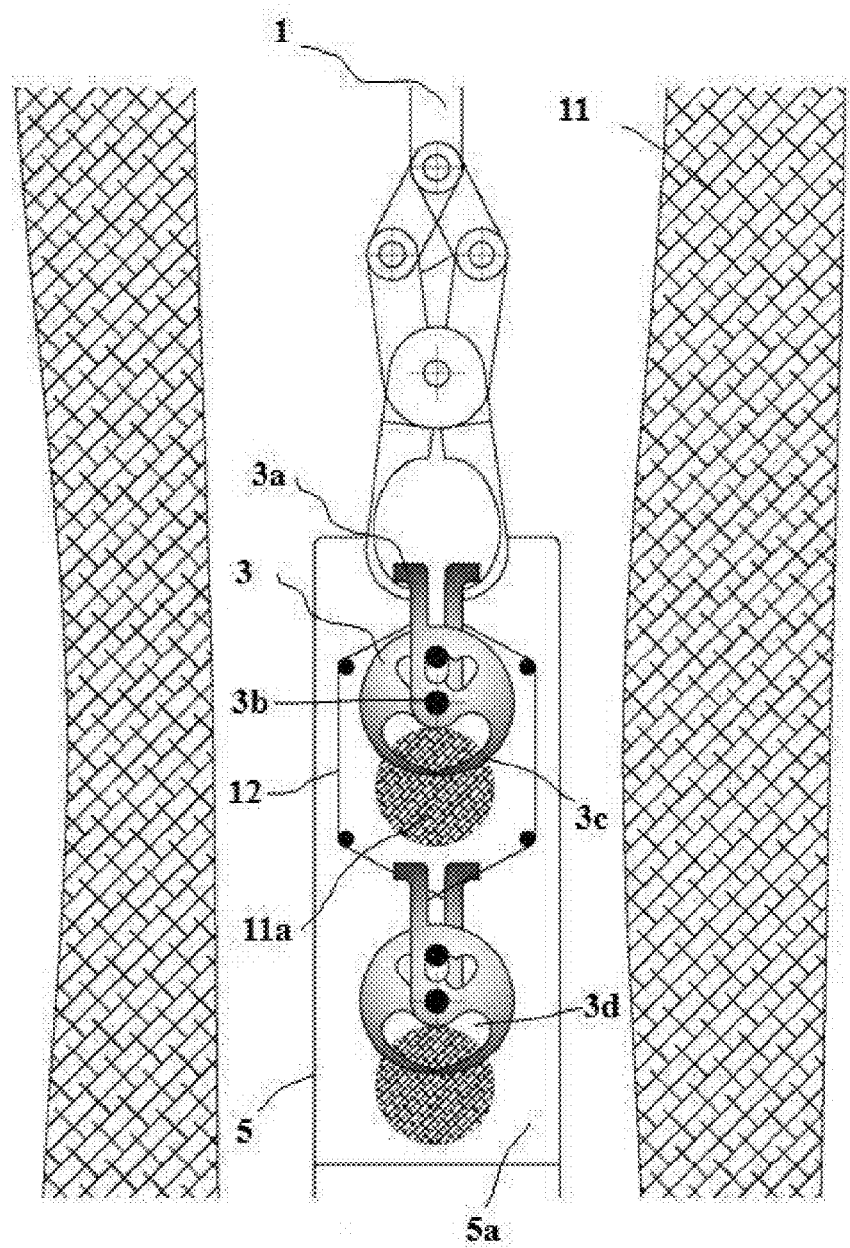
FIG. 4 illustrates one embodiment of the invention, in which several sets of clamping brackets work together to cause a fixing device to clamp on the surface of a tissue.

FIG. 4 illustrates one embodiment of the invention, in which several sets of clamping brackets work together to cause the fixing device to clamp on the surface of the tissue 11.

Figure 5A:
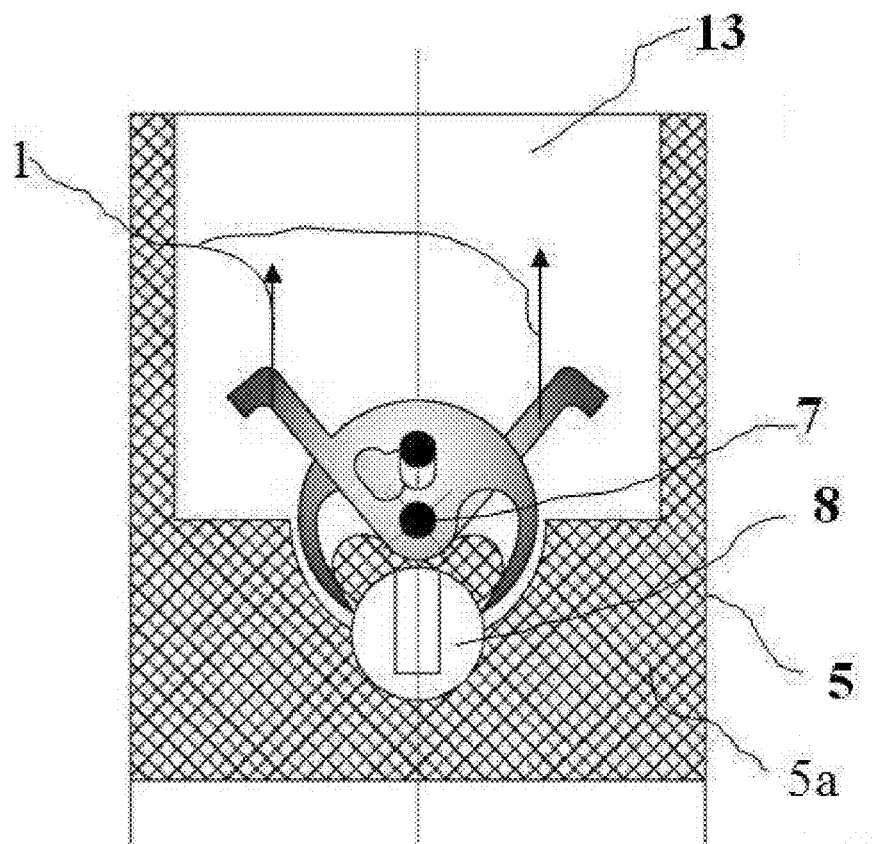
FIG. 5a and FIG. 5b illustrate a structure of a fixing mechanism of one embodiment of the invention.
Figure 5B:
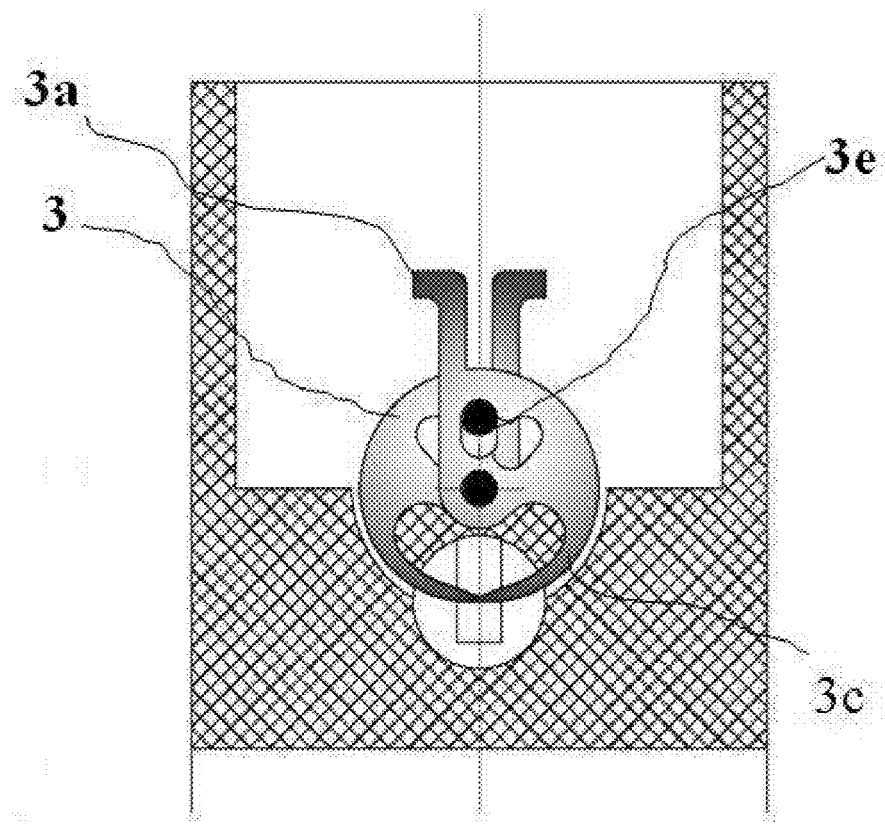
Figure 6:
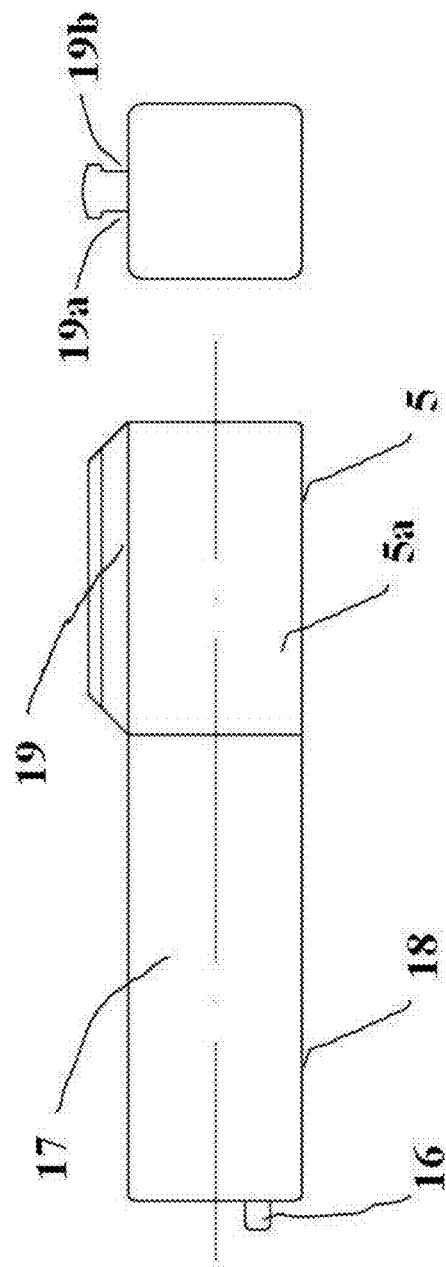
FIG. 6 illustrates the structure of a fixing device of another embodiment of the invention.

FIG. 6 illustrates the structure of the fixing device of another embodiment of the invention. The fixing device comprises a base 18, and a fixing mechanism 5 in fixed connection with the base 18. FIG. 5 and FIG. 1-FIG. 4 illustrate the structure of the fixing mechanism 5.

Referring to FIG. 5a and FIG. 5b, the fixing mechanism 5 comprises a housing 5a and at least a set of clamping brackets 3 and a rotating shaft 7; a bracket hole 3b is formed on each clamp bracket 3, and the rotating shaft 7 passes through the bracket hole 3b and fixes each set of the clamping brackets on the housing 5a of the fixing device; a passage 13 is formed on the housing 5a for allowing the entry and exit of a force acting mechanism 1, and a through hole 8 is formed on the housing 5a for allowing gas to enter the fixing device;

Referring to FIG. 1-FIG. 5b, when the fixing device for intravital lumen is placed inside an intravital lumen 11, the gas is extracted through the through hole 8, and a soft tissue 11a of intravital lumen enters a clearance space 3d between a pair of the clamping brackets 3, and a force is acted on the back ends of at least a pair of the clamping bracket 3 and causes the clamping brackets 3 to rotate around the rotating shaft 7; and with the rotation of the clamping brackets 3, the opening degree of two front ends of a pair of clamping brackets 3 becomes smaller, which causes the soft tissue in the clearance space 3d to be squeezed and clamped; when the clamping brackets 3 clamp, an intravital tissue is squeezed and enclosed in a small space, which causes the fixing device to be fixed on the wall of intravital tissue.

Referring FIG. 2 and FIG. 3a, each of the clamping brackets 3 further comprises a stop mechanism 3e disposed thereon; when the clamping brackets 3 clamp, the intravital tissue is squeezed and enclosed in a small space, meanwhile, the clamping brackets 3 are locked by the stop mechanism 3e.

Referring to FIG. 2, a force acted on back ends of the clamping brackets is generated by the force acting mechanism 1. The force acting mechanism 1 may be a general force acting mechanism such as movable arms of endoscope biopsy forceps, and may also be a dedicated force acting mechanism, in this embodiment, and there is no limitation to the type of force acting mechanism; referring to FIG. 3, a force acted on back ends 3a of the clamping brackets is generated by a medical string 12.

Referring to FIG. 3b, the fixing device further comprises a compression spring 27 connected to the back ends of a pair of the clamping brackets 3 and a stop bolt 26, when the fixing device is in initial state thereof and placed outside the intravital lumen, one segment of the stop bolt 26 stays in a first stop hole 26a formed on the housing 5a and another segment of the stop bolt 26 stays in a second stop hole 26b formed on each clamping bracket; the compression spring 27 is in compression state, and the front ends of a pair of clamping brackets 3 are at opening position thereof; after the fixing device is placed inside the intravital lumen, the gas is extracted through the through hole 8, and the soft tissue 11a of the intravital lumen enters the clearance space 3d; a tension force generated by the compression spring 27 is acted on the back ends 3a after the stop bolt 26 is pulled out from the first stop hole 26a and the second stop hole 26b, which closes the back ends 3a of the clamping brackets, causes two front ends 3c of a pair of clamping brackets to rotate around the rotating shaft 7 and clamp, and causes the intravital tissue to be squeezed and enclosed in the clearance space 3d, thereby fixing the fixing device on the wall of the intravital tissue. In this embodiment of the invention, the compression spring 27 can be considered as the stop mechanism 3e.

In addition, when the fixing mechanism 5 comprises a set of clamping brackets 3, each set of clamping brackets comprises at least a pair of clamping brackets; when the fixing mechanism 5 comprises at least two sets of clamping brackets 3, each set of clamping brackets comprises one or more pairs of clamping brackets 3; and the back ends 3a of all the clamping brackets 3 are connected to each other through a medical string 12, in order to work together under an acting force (referring to FIG. 4).

It still refers to FIG. 6 that the base 18 may comprise a detecting head for data acquisition or a treating mechanism 16, and a wireless transmission unit 17; the detecting head or a treating mechanism 16 is connected with the wireless transmission unit 17, and is exposed outside the fixing device. The acquisition data are transmitted to the outside of the fixing device through the wireless transmission unit 17.

Figure 7:
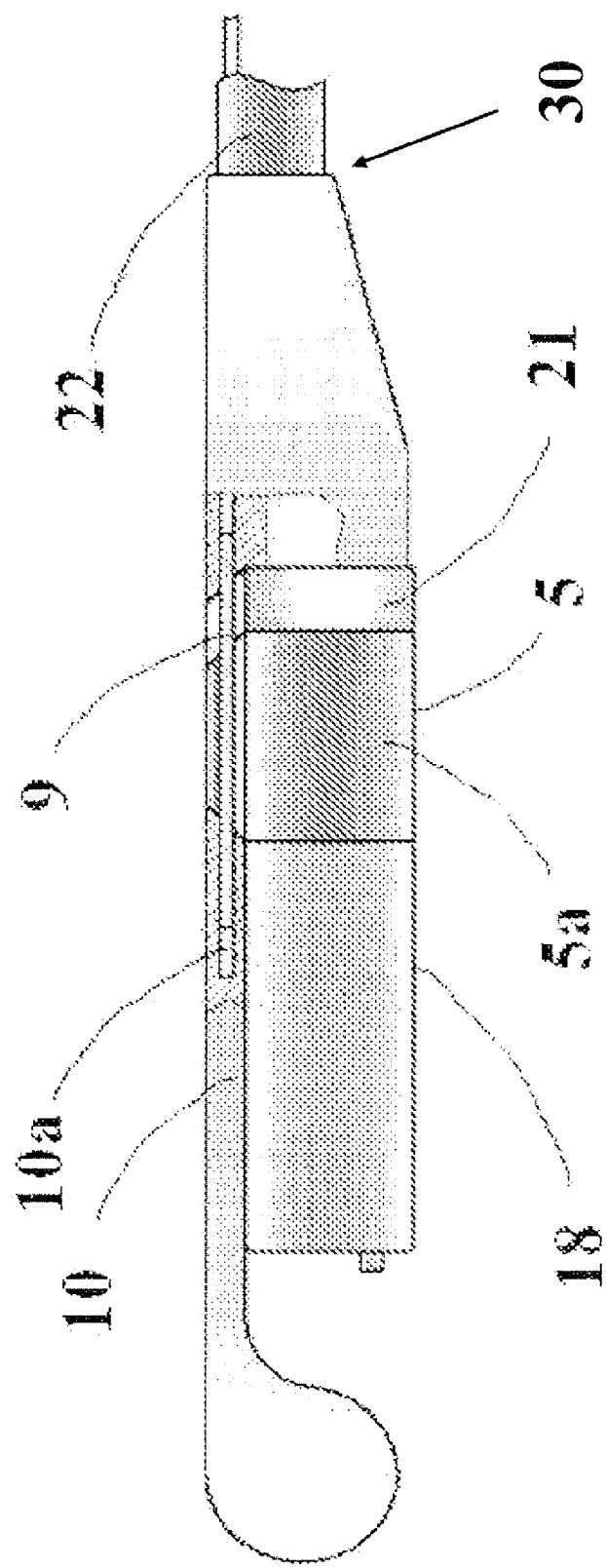
FIG. 7 illustrates one embodiment of the invention, in which a fixing device is fixed on a releasing means.

Referring to FIG. 6 and FIG. 7, the fixing device may further comprise a releasing seat 19, through which the fixing mechanism 5 is fixed on a releasing means 30.

Figure 8:
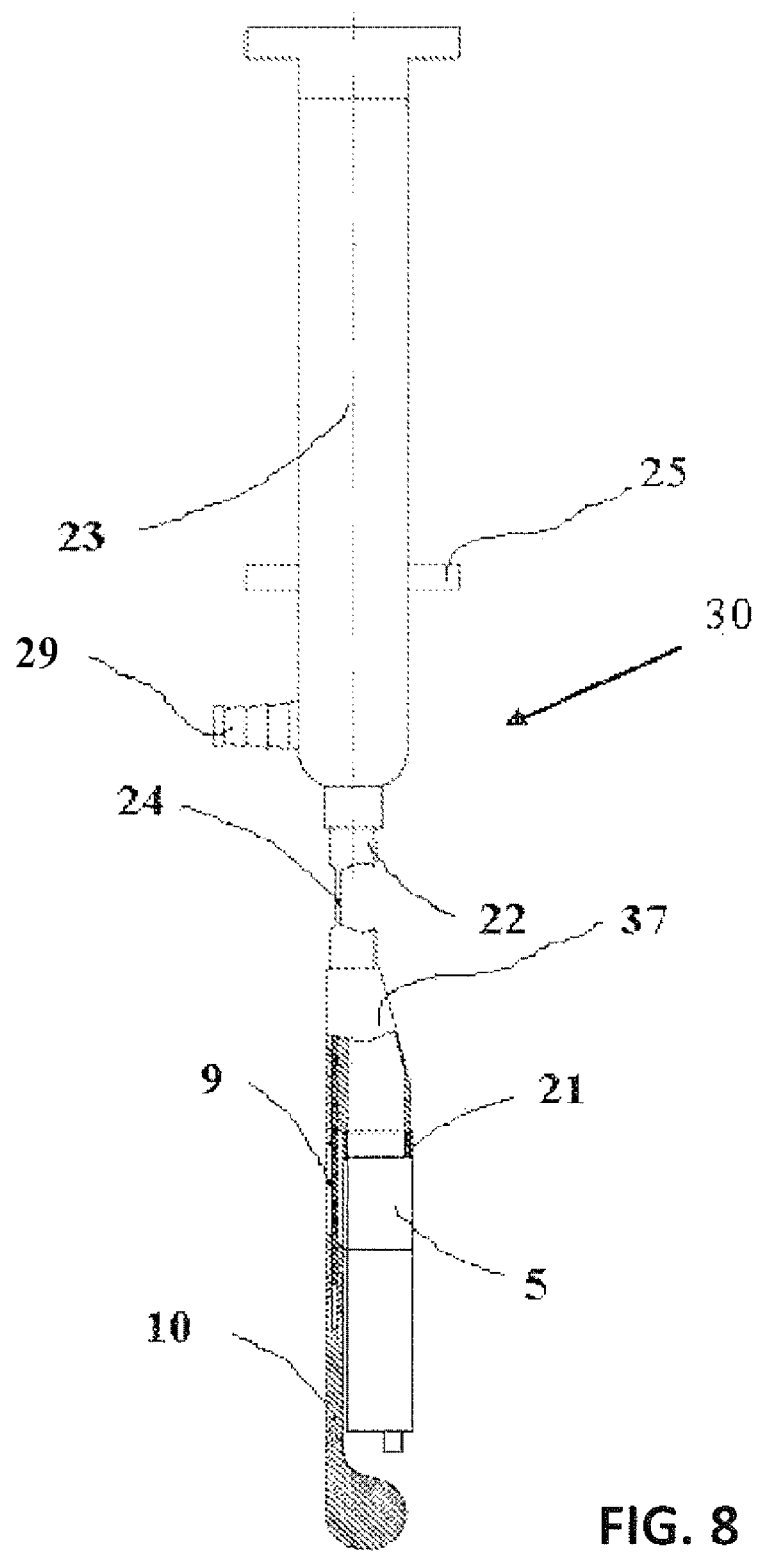
FIG. 8 illustrates the structure of a releasing means of one embodiment of the invention.

FIG. 7 illustrates one embodiment of the invention, in which the fixing device is fixed on the releasing means 30;

FIG. 8 illustrates a structure of the releasing means 30 of one embodiment of the invention.

Figure 9:
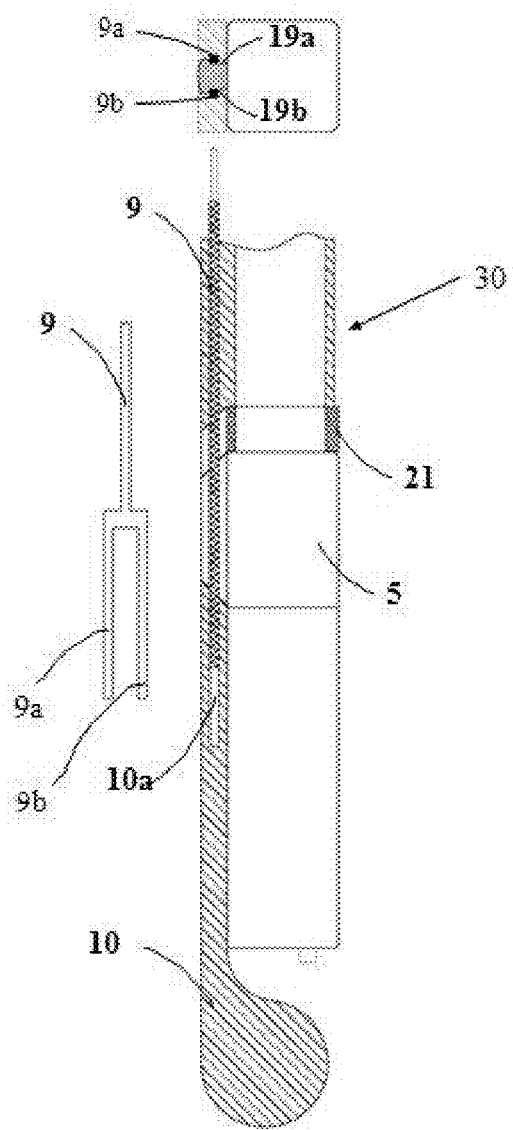
FIG. 9 illustrates one embodiment of the invention, in which a fixing device is fixed on a releasing means.

FIG. 9 illustrates one embodiment of the invention, in which the fixing device is fixed on the releasing means 30.

Referring to FIG. 7 to FIG. 9, the releasing means 30 comprises a connecting seat 10, a sealing washer 21, a guiding pipe 22, a clamping mechanism 9, a handle 23 having a movable operating bolt 25, and a gas inlet 29; the gas inlet 29 is adapted for extracting the gas from the through hole 8 through the passage 13 (as shown in FIG. 5a); the guiding pipe 22 is connected with the handle 23; a movable force acting string 24 passes through the guiding pipe 22 and the sealing washer 21 and is further fixed on a sealing seat 37; the sealing seat 37 is connected with the clamping mechanism 9; the clamping mechanism 9 is embedded in the connecting seat 10, and the connecting seat 10 comprises a sliding groove 10a which allows the clamping mechanism 9 to slide in.

The detailed course of extracting the gas from the through hole 8 through the passage 13 using the gas inlet 29 is described as below:

as the passage 13 is formed on the housing 5a of the fixing mechanism 5 and the fixing mechanism 5 is connected with the releasing means 30 (referring to FIG. 8), the passage 13 is in sealed connection with the sealing washer 21 of the releasing means 30, the gas is extracted from the through hole 8 through the gas passage formed by the gas inlet 29 and the guiding pipe 22 of the releasing means 30.

Referring to FIG. 9, the clamping mechanism 9 may comprise at least a pair of transformable or movable clamping clacks 9a and 9b; the clamping clacks 9a and 9b are in movable connection with two grooves 19a and 19b of the releasing seat 19; and the fixing mechanism 5 is fixed on the connecting seat 10 through the releasing seat 19 and the clamping mechanism 9; a relative movement is formed between the clamping mechanism 9 and the connecting seat 10, which causes the clamping clacks 9a and 9b to be disengaged from the grooves 19a and 19b of the releasing seat 19 and further causes the releasing means 30 to be disengaged from the fixing mechanism 5, thereby releasing the fixing mechanism 5.

FIG. 10a-FIG. 10f illustrate several structures for allowing a relative movement between the clamping mechanism 9 and the connecting seat 10.

Figure 10A:
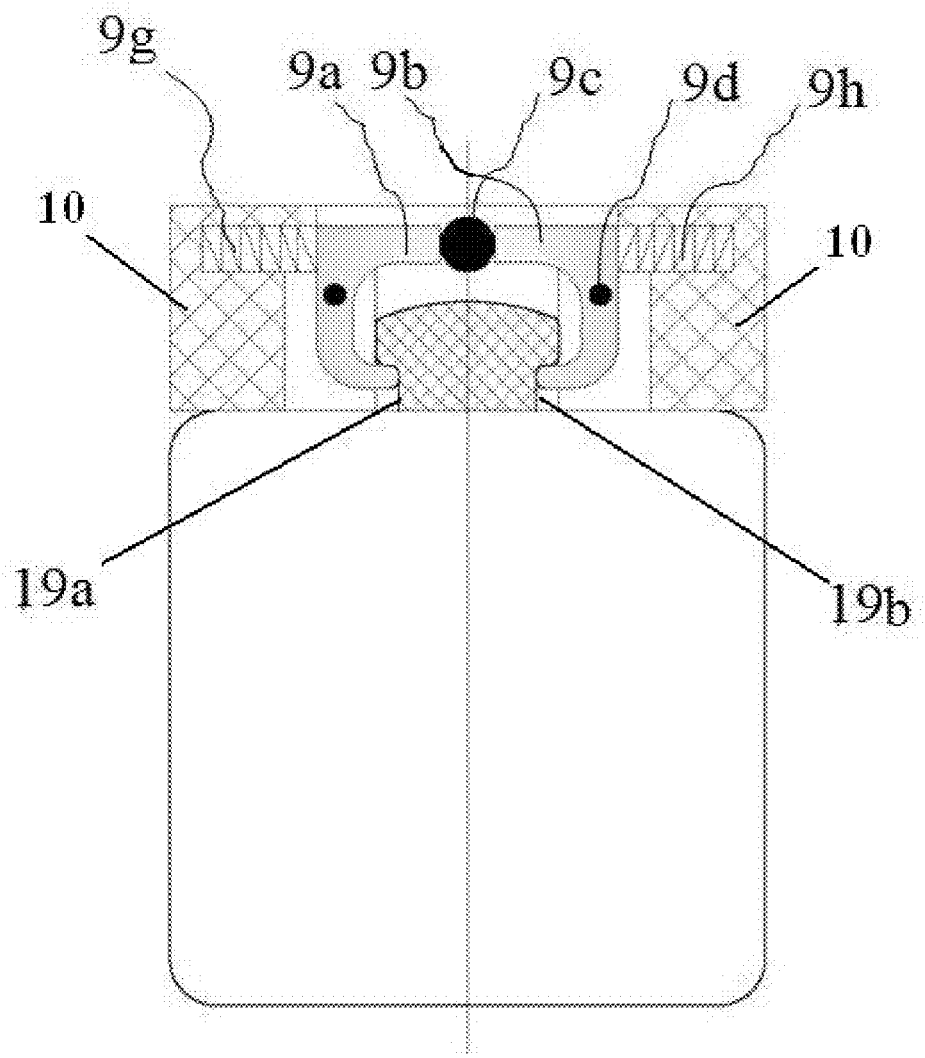
FIG. 10a-FIG. 10f illustrate several structures allowing a relative movement between a clamping mechanism and a connecting seat; and FIG. 11a-FIG. 11f illustrates different states of a fixing device, such as clamping, releasing, and being fixed on a tissue.
Figure 10B:
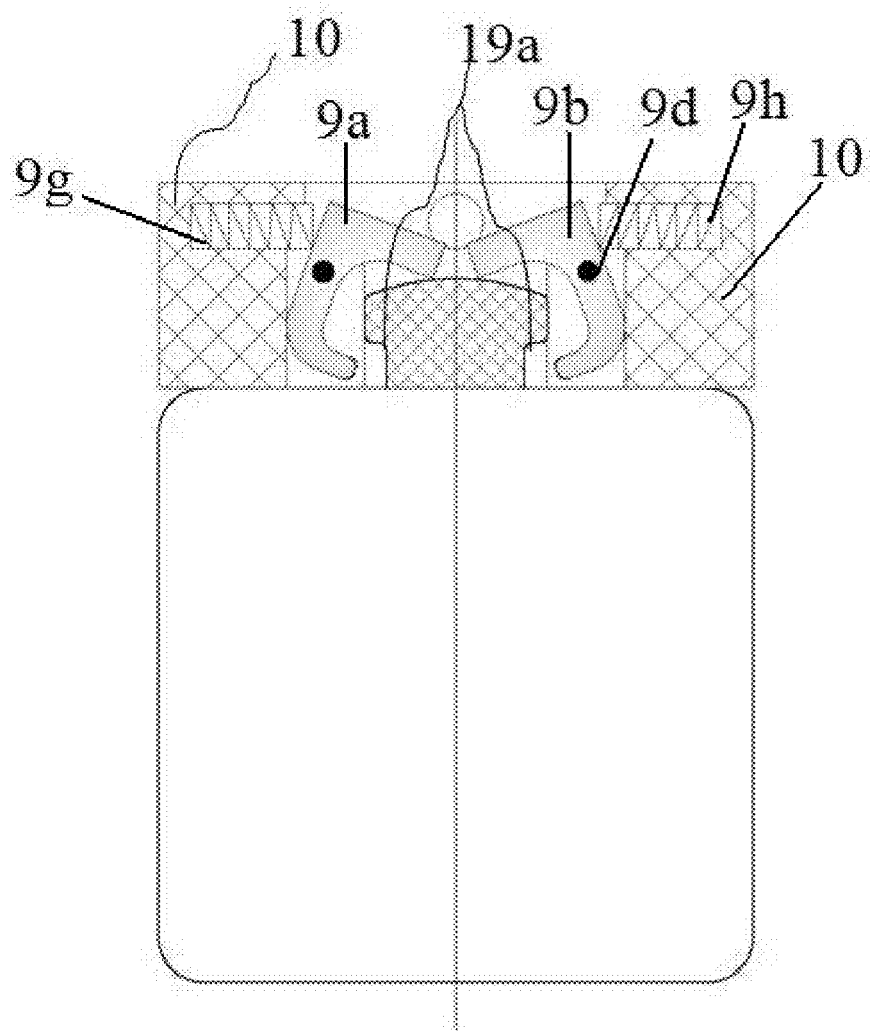

Referring to FIG. 10a and FIG. 10b, the clamping mechanism 9 further comprises a fixing shaft 9d, a supporting shaft 9c, a first releasing spring 9g, and a second releasing spring 9h; the clamping clacks 9a and 9b are fixed on the connecting seat 10 through the fixing shaft 9d; one end of the first releasing spring 9g is fixed on the releasing seat 10, while the other end of the first releasing spring 9g is fixed on one clamping clack 9a; and one end of the second releasing spring 9h is fixed on the releasing seat 10, while the other end of the second releasing spring 9h is fixed on another clamp clack 9b; after a supporting shaft 9c is extracted, the clamping clacks 9a,9b are pushed by releasing springs 9g and 9h and rotate around the fixing shaft 9d, which enlarges the gap between the clamping clacks 9a and 9b causes the clamping clacks 9a and 9b to be disengaged from the grooves 19a and 19b.

Figure 10C:
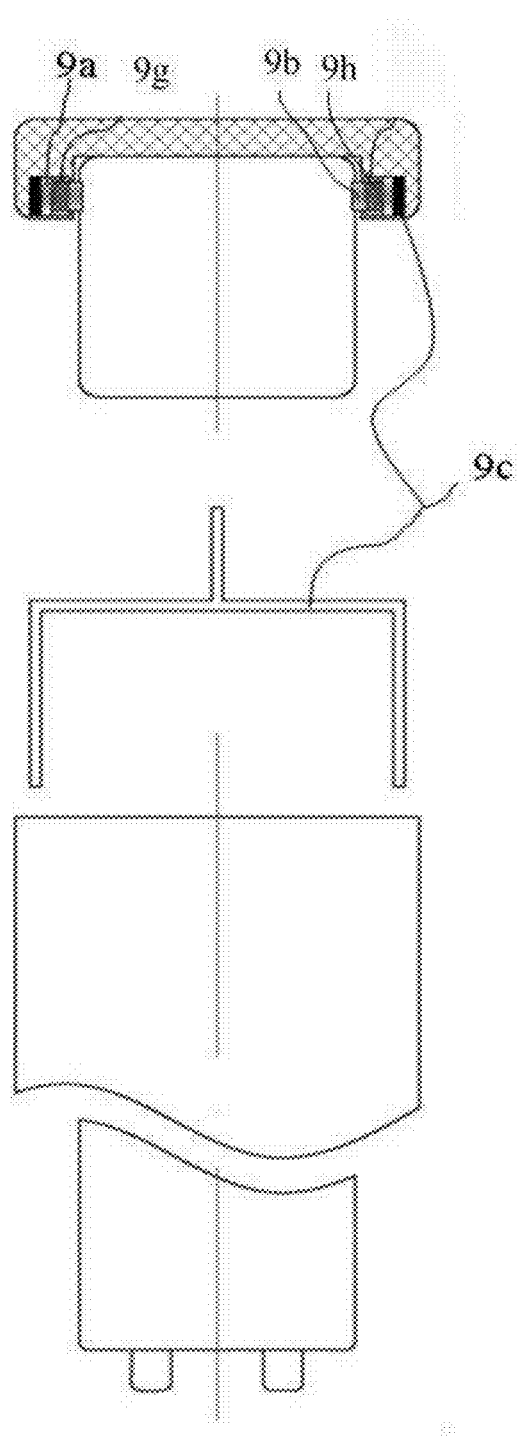
Figure 10D:
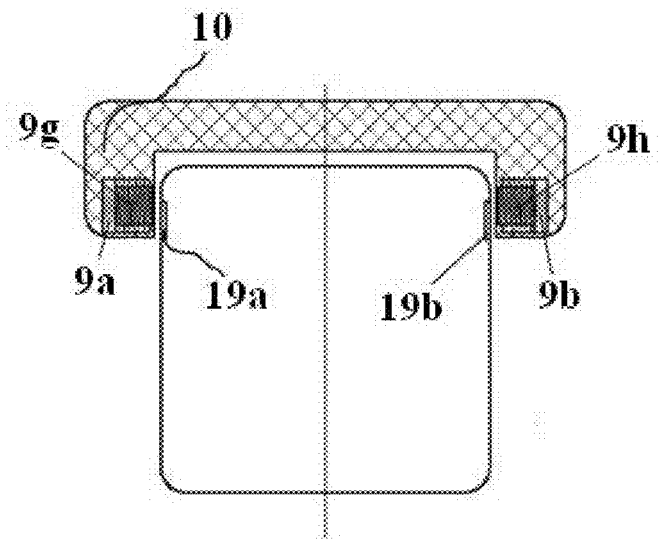

Referring to FIG. 10c and FIG. 10d, the clamping mechanism 9 further comprises a supporting shaft 9c, a first releasing spring 9g, and a second releasing spring 9h; the clamping clacks 9a, 9b are fixed on the connecting seat 10 through a supporting shaft 9c and releasing strings 9g, 9h; after the supporting shaft 9c is extracted, the clamping clacks 9a and 9b may be pushed by the releasing strings 9g, 9h and move towards the connecting seat 10, which enlarges the gap between the clamping clacks and causes the clamping clacks to be disengaged the grooves 19a and 19b.

Figure 10E:
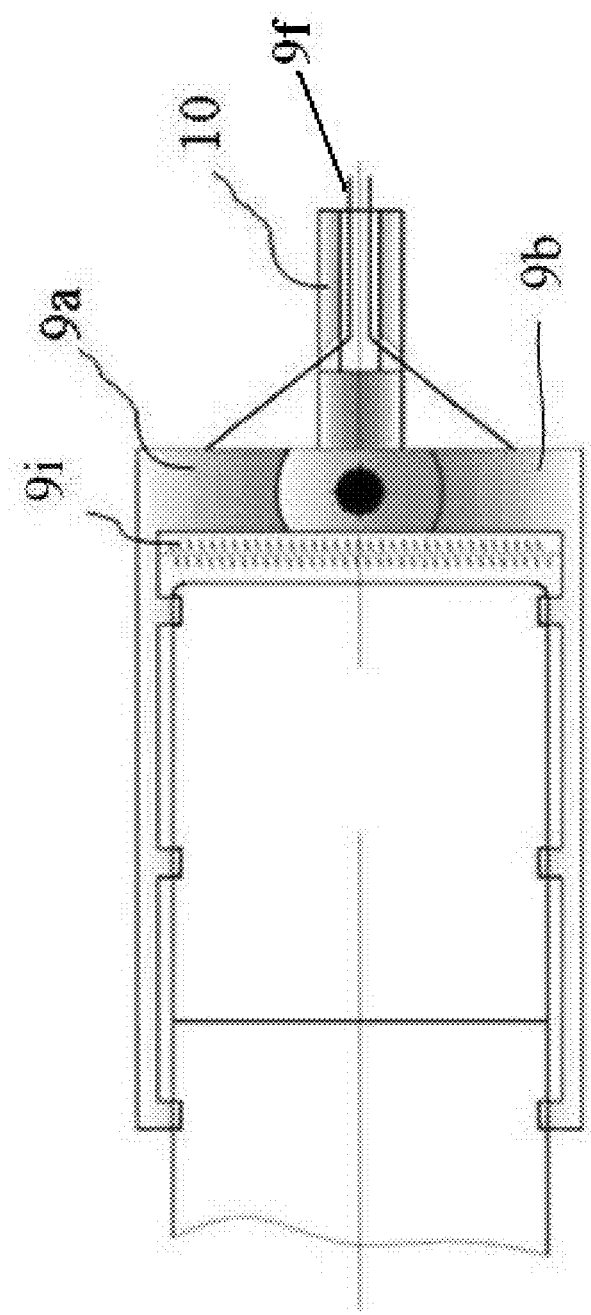
Figure 10F:
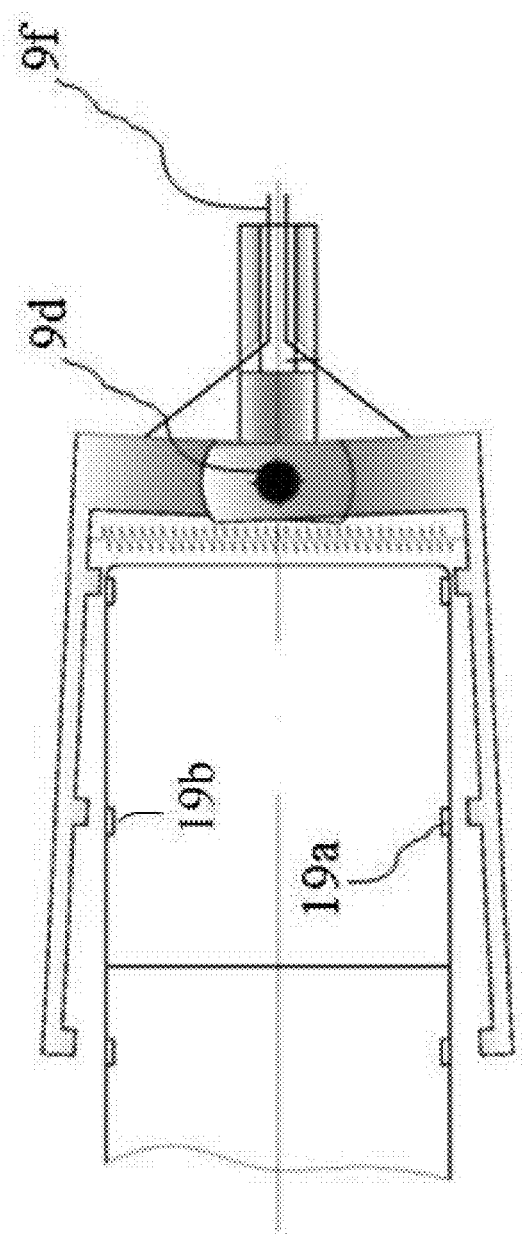

Referring to FIG. 10e and FIG. 10f, the clamping mechanism 9 further comprises a fixing shaft 9d, pulling component 9f, and releasing spring 9i; the clamping clacks 9a and 9b are fixed on the connecting seat 10 through the fixing shaft 9d; and when the pulling component 9f is pulled, the clamping clacks 9a and 9b start to rotate around the fixing shaft 9d, which enlarges the gap between the clamping clacks 9a and 9b and causes the clamping clacks 9a and 9b to be disengaged from the grooves 19a and 19b.

Figure 11A:
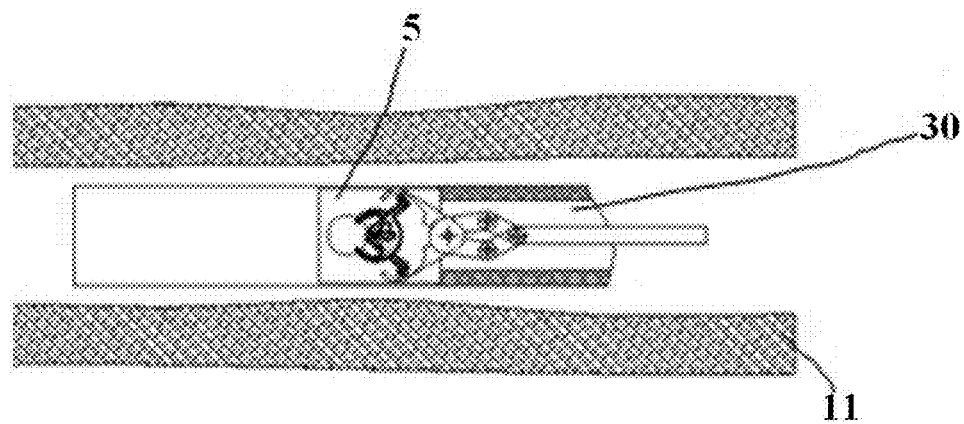
Figure 11B:
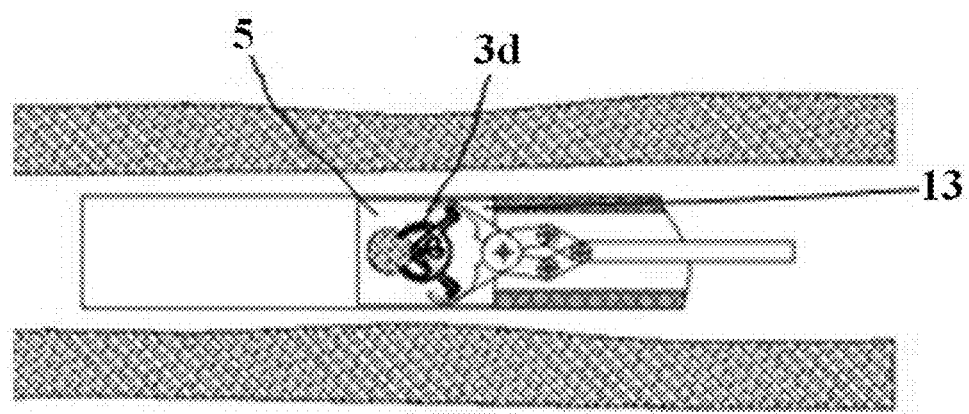
Figure 11C:
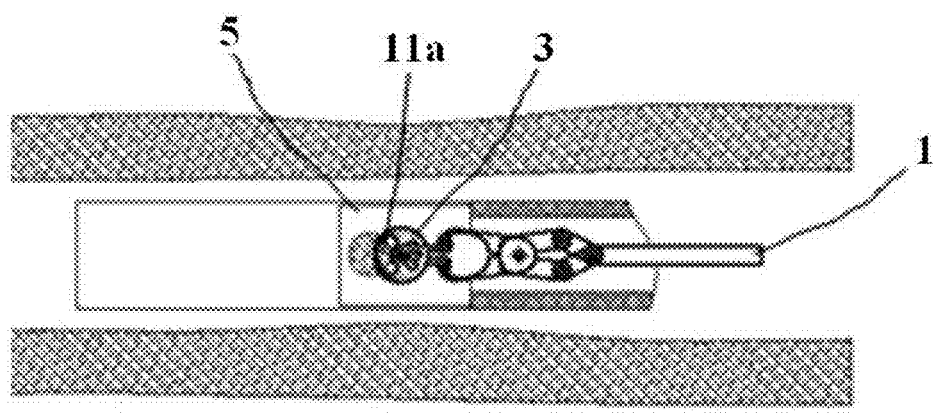
Figure 11D:
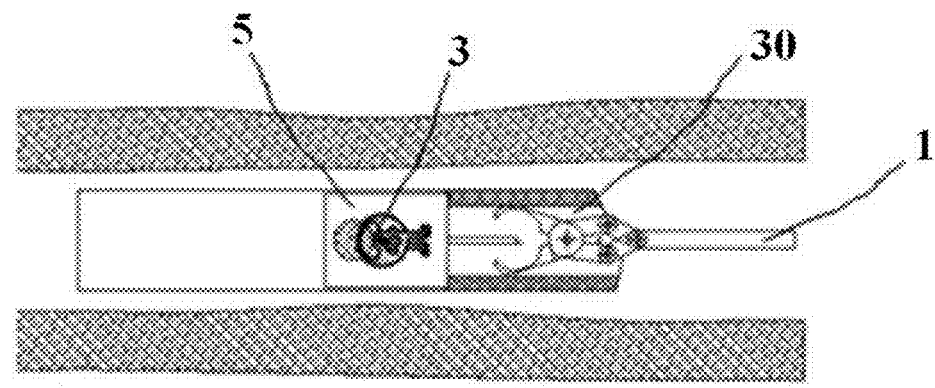
Figure 11E:
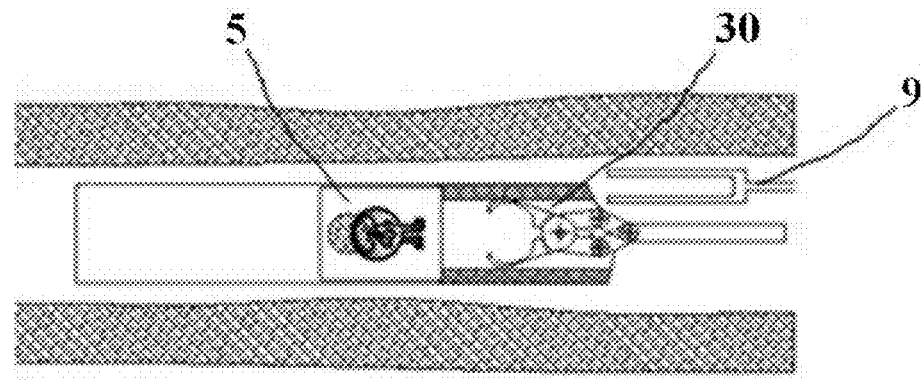
Figure 11F:
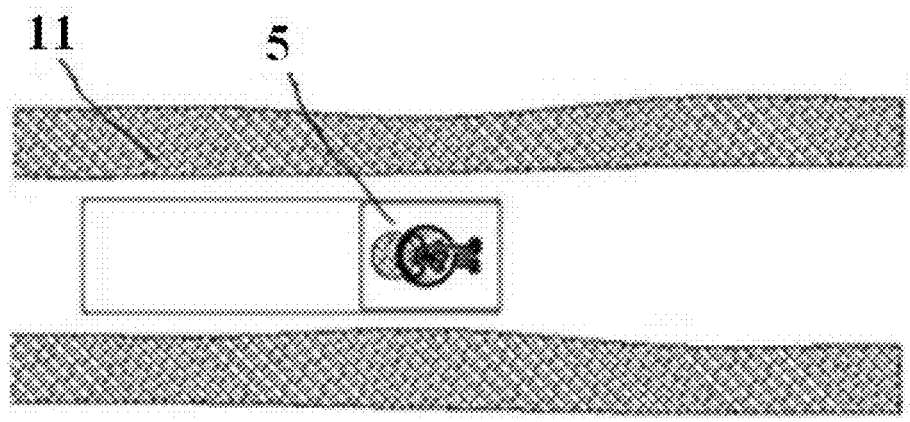

FIG 11a to FIG. 11f illustrate different states of the fixing mechanism 5, such as clamping, releasing, and being fixed on the tissue. Referring to FIG. 11a, the fixing device of the invention enters the lumen of intravital tissue 11 under the guidance of the releasing means 30, and attaches to the wall of the lumen; referring to FIG. 11b, the gas is extracted from the passage 13, which causes the wall of lumen 11 to enter the clearance space 3d; referring to FIG. 11c, the clamping brackets 3 are operated by a force acting mechanism 1 so as to clamp and squeeze the intravital tissue 11a, which encloses the intravital tissue 11a in the clearance space 3d, thereby causing the fixing device to be fixed on the intravital tissue 11a; referring to FIG. 11d, it illustrates the separation of the clamping brackets 3 from the force acting mechanism 1; referring to FIG. 11e, the clamping mechanism 9 of the releasing mechanism 30 is disengaged from the releasing seat 19 of the fixing device, which causes the fixing device to be disengaged from the releasing mechanism 30; referring to 11f, after the fixing device leaves the releasing mechanism 30, it clamps the tissue 11, which causes the fixing device to be fixed on tissue 11.

In the embodiments of the invention, the device is fixed at multiple points on the wall of intravital lumen, which provides a restriction to the axial rotation of such device in the lumen, enhances the reliability of fixation, and improves the accuracy of locating of device.

It will be noted that the term "comprises/comprising" as used in this description is intended to denote the presence of a given characteristic, step or component, without excluding the presence of one or more other characteristic, features, integers, steps, components or groups thereof. While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A fixing device, comprising:
   a) a base; and
   b) a fixing mechanism fixed on said base;
      wherein
         said fixing mechanism comprises
            a housing,
            at least a set of clamping brackets, and
            a rotating shaft;
      a bracket hole is formed on each clamp bracket, and said rotating shaft passes through said bracket hole and fixes each set of said clamping brackets on the housing of said fixing device; a passage is formed on said housing for allowing the entry and exit of a force acting mechanism, and a through hole is formed on said base for allowing gas to enter said fixing mechanism;
      when said fixing device for intravital lumen is placed inside an intravital lumen, the gas is extracted through said through hole, a soft tissue of intravital lumen enters a clearance space between a pair of said clamping brackets, and a force is acted on back ends of at least a pair of said clamping brackets and causes said clamping brackets to rotate around said rotating shaft;
      with the rotation of said clamping brackets, the opening degree of two front ends of a pair of said clamping brackets becomes smaller, which causes said soft tissue in said clearance space to be squeezed and clamped;
      when said clamping brackets clamp, an intravital tissue is squeezed and enclosed in a small space, which causes said fixing device to be fixed on the wall of intravital tissue;
      the fixing device further comprises a compression spring connected to said back ends of a pair of said clamping brackets and a stop bolt,
      wherein a first stop hole is formed on said housing, and a second stop hole is formed on each said clamping bracket;
      when said fixing device is placed outside the intravital lumen, said stop bolt stays in both a first stop hole and a second stop hole; said compression spring is in compression state, and two front ends of a pair of said clamping brackets are at opening position thereof; and
      after said fixing device is placed inside said intravital lumen, the gas is extracted through said through hole and said soft tissue of said intravital lumen enters said clearance space; a tension force generated by said compression spring is acted on said back ends after said stop bolt is pulled out from said first stop hole and said second stop hole, which closes said back ends of said clamping brackets, causes two front ends of a pair of said clamping brackets to rotate around said rotating shaft and clamp, and causes said intravital tissue to be squeezed and enclosed in said clearance space and further causes said fixing device to be fixed on the wall of said intravital tissue.

2. The fixing device of claim 1, wherein
   when said fixing mechanism comprises a set of clamping brackets, each set of clamping brackets comprises at least a pair of clamping brackets;
   when said fixing mechanism comprises at least two sets of clamping brackets, each set of clamping brackets comprises one or more pairs of clamping brackets; and said back ends of all said clamping brackets are connected to each other through a medical string, in order to work together under an acting force.

3. The fixing device of claim 1, wherein
   said base comprises a detecting head for data acquisition or a treating mechanism, and a wireless transmission unit, said detecting head or treating mechanism is in fixed connection with said wireless transmission unit and is exposed outside said fixing device.

4. The fixing device of claim 1, wherein further comprising a releasing seat, through which said fixing mechanism is fixed on a releasing means.

5. The fixing device of claim 4, wherein
said releasing means comprises a connecting seat, a sealing washer, a guiding pipe, a clamping mechanism, and a handle;
a movable operating bolt and a gas inlet are disposed on said handle;
said guiding pipe is connected with said handle;
a movable force acting string passes through said guiding pipe and said sealing washer to be fixed on a sealing seat;
said sealing seat is connected with said clamping mechanism;
said clamping mechanism is embedded in said connecting seat; and
said connecting seat comprises a sliding groove which allows said clamping mechanism to slide in.

6. The fixing device of claim 5, wherein
said clamping mechanism comprises at least two transformable or movable clamping clacks;
said clamping clacks are in movable connection with two grooves of said releasing seat;
said fixing mechanism is fixed on said connecting seat through said releasing seat and said clamping mechanism; and
a relative movement is formed between said clamping mechanism and said connecting seat, which causes said clamping clacks to be disengaged from said grooves of said releasing seat and further causes said releasing means to be disengaged from said fixing mechanism, thereby releasing said fixing mechanism.

7. The fixing device of claim 6, wherein
said clamping mechanism further comprises a fixing shaft, a supporting shaft, a first releasing spring, and a second releasing spring;
said clamping clacks are fixed on said connecting seat through said fixing shaft; and
after a supporting shaft is extracted, said clamping clacks are pushed by releasing springs and rotate around said fixing shaft, which enlarges the gap between said clamping clacks and causes said clamping clacks to be disengaged from said grooves.

8. The fixing device of claim 6, wherein
said clamping mechanism further comprises a supporting shaft, a first releasing spring, and a second releasing spring;
said clamping clacks are fixed on said connecting seat through a supporting shaft and releasing strings; and
after said supporting shaft is extracted, said clamping clacks are pushed by said releasing strings and move towards said connecting seat, which enlarges the gap between said clamping clacks and causes said clamping clacks to be disengaged from said grooves.

9. The fixing device of claim 6, wherein
said clamping mechanism further comprises a fixing shaft, pulling component, and releasing spring; said clamping clacks are fixed on said connecting seat through said fixing shaft; and
when said pulling component is pulled, said clamping clacks start to rotate around said fixing shaft, which enlarges the gap between said clamping clacks and causes said clamping clacks to be disengaged from said grooves.

* * * * *